(12) United States Patent
Ekman-Ordeberg et al.

(10) Patent No.: US 8,207,145 B2
(45) Date of Patent: *Jun. 26, 2012

(54) USE OF SULFATED GLYCOSAMINOGLYCANS FOR ESTABLISHING EFFECTIVE LABOR IN WOMEN

(75) Inventors: Gunvor Ekman-Ordeberg, Danderyd (SE); Anders Malmström, Lund (SE)

(73) Assignee: Dilafor AB, Stockholm (SE)

( * ) Notice: Subject to any disclaimer, the term of this patent is extended or adjusted under 35 U.S.C. 154(b) by 284 days.

This patent is subject to a terminal disclaimer.

(21) Appl. No.: 12/168,683

(22) Filed: Jul. 7, 2008

(65) Prior Publication Data

US 2008/0269165 A1  Oct. 30, 2008

Related U.S. Application Data

(63) Continuation of application No. 10/500,284, filed as application No. PCT/SE03/00004 on Jan. 2, 2003, now Pat. No. 7,407,945.

(30) Foreign Application Priority Data

Jan. 2, 2002 (SE) ...................................... 0200005

(51) Int. Cl.
A61K 31/727 (2006.01)
A61K 31/737 (2006.01)

(52) U.S. Cl. .......................................... 514/56; 514/54

(58) Field of Classification Search .................. None
See application file for complete search history.

(56) References Cited

U.S. PATENT DOCUMENTS 5,714,477 A  2/1998 Einarsson

FOREIGN PATENT DOCUMENTS

| EP | 0 302 034 B1 | 4/1993 |
|---|---|---|
| EP | 0867452 A1 | 9/1998 |
| EP | 1016410 A1 | 7/2000 |
| JP | 62-19520 A | 1/1987 |
| JP | 11-310602 A | 11/1999 |
| JP | 2000-309544 A | 11/2000 |
| WO | WO-92/17187 A1 | 10/1992 |

OTHER PUBLICATIONS

Walker, J. "Pre-eclampsia" The Lancet (2000) vol. 356, pp. 1260-1265.*
Osmers et al., "Glycosaminoglycans in Cervical Connective Tissue During Pregnancy and Parturition", Obstetrics & Gynecology, vol. 81, No. 1, Jan. 1998, pp. 88-92.
Ginsberg, J. et al., "Use of antithrombotic agents during pregnancy" Chest (2001) vol. 119, No. 1, pp. 122S-129S.
Sanson et al. "Safety of Low-Molecular-Weight Heparin in Pregnancy . . . " Thromb. Haem. (1999) vol. 81, pp. 668-672.
Ellison et al. "Use of enoxaparin in a pregnant woman . . . " Br. J. Obst. Gyn. (2001) vol. 108, pp. 757-759.
Greinacher et al. "Pregnancy complicated by heparin associated thrombocytopenia . . . " Thromb. Res. (1993) vol. 71, pp. 123-126.
British Medical Journal, Nov. 16, 1974. K. Shaker et al., "Uterine Contractions Due to Heparin", pp. 408-409.
Obstet Gynecol, vol. 81, 1993, Rudiger Osmers et al., "Glycosaminoglycans in Cervical Connective Tissue During Pregnancy and Parturition", pp. 88-92.

* cited by examiner

*Primary Examiner* — Leigh Maier
(74) *Attorney, Agent, or Firm* — Birch, Stewart, Kolasch & Birch, LLP

(57) ABSTRACT

The invention refers to the use of sulfated glycosaminoglycans having an anticoagulant activity of 100 BP units/mg or less for the manufacture of a pharmaceutical preparation for prophylactic priming or curative treatment of the cervix and the myometrium for establishing effective labor in women.

12 Claims, No Drawings

USE OF SULFATED GLYCOSAMINOGLYCANS FOR ESTABLISHING EFFECTIVE LABOR IN WOMEN

This application is a Continuation of U.S. application Ser. No. 10/500,284 filed on Jul. 1, 2004 now U.S. Pat. No. 7,407,945 which is the national phase of PCT International Application No. PCT/SE03/00004 filed on Jan. 2, 2003, which designated the United States, and on which priority is claimed under 35 U.S.C. §120. This application also claims priority under 35 U.S.C. §119(a) on Patent Application No(s). 0200005-7 filed in Sweden on Jan. 2, 2002. The entire contents of each of the above documents is hereby incorporated by reference.

The present invention refers to the use of certain sulfated glycosaminoglycans for the manufacture of a pharmaceutical composition for the prevention and treatment of slow progress of term labor.

BACKGROUND

A common clinical problem in obstetrics is prolonged or in some way dysfunctional labor. Slow progress or arrest of labor is documented in about 40-60% of all parturitions in Sweden. In developing countries maternal deaths due to labor arrest with heavy post partum bleedings are the most common reasons for maternal deaths. Slow progress of labor is the most common indication for emergency caesarian section, which in turn often results in a demand for elective caesarian section at the next pregnancy. Other complications of protracted labor generate increased fetal asphyxia resulting in long-term sequele.

The uterus is composed of two parts, the corpus and the cervix having different functions during pregnancy and parturition. The corpus uteri consist predominantly of smooth muscle bundles, the myometrium, embedded in extra cellular matrix, ECM, and the cervix consists mainly of ECM. The dominating components of the ECM are the collagens, but there are also proteoglycans albeit in a smaller quantity. Proteoglycans consist of a protein core to which one to a hundred polysaccharide chains, the glycosaminoglycans, are attached.

The coordination between the uterine contractions and the softening, or in other words ripening, and dilation of the cervix is crucial for a normal parturition. Incongruity between these processes leads to abnormal parturitions.

During pregnancy and labor both the cervix and the corpus are remodeled. A profound remodeling of the corpus results in an approximately seven-fold increase in volume. An insufficient uterine remodeling is related to a disturbed contractility. A normal dilation of the cervix opening from 1 to 10 cm during established labor implies a total reconstruction of the cervical connective tissue generated through a decrease of the concentration of collagen and proteoglycans and resulting in a soft and elastic cervix. Disturbances in the cervical ripening can, if the process starts too early, result in a pre-term delivery. Pre-term labor must be coordinated with a pre-term cervical ripening in order to give a premature delivery. On the other hand insufficient cervical ripening results in post-term pregnancy with high frequency of protracted labor and instrumental deliveries. Thus the cervical ripening and myometrial contractions are two processes, which must be coordinated to accomplish a normal delivery.

The physiology of both normal and protracted labor is still obscure. The hormonal control seems to include an inhibitory effect by progesterone and activation by increasing estrogen levels. Corticotrophin releasing hormone, prostaglandin and a changed estrogen/progesterone ratio has been suggested to be involved in the initiation of labor. Intravenous infusion of oxytocin, introduced in 1950, is still the dominating treatment of protracted labor and recently published investigations and review articles on slow progress of labor mainly present different treatment schedules of oxytocin administration. This treatment fails in many cases and results in an increasing number of operative deliveries. There have been few efforts to develop new drugs for labor augmentation despite a tremendous global problem of slow progress of labor.

Induction of labor in women with unfavorable cervices has been performed by local application of prostaglandin E2 for about twenty years. In 15-20% of said cases cervical ripening and labor induction fail. Most prominent is arrest of labor.

PRIOR ART

Uterine contractions due to heparin are described as a side effect of intravenous administration of high-dose of heparin for the treatment of vein thrombosis to a 32 year old multigravida in the thirty-second week of pregnancy, by K. Shaker et al., British Medical Journal 16 Nov. 1974. Heparin is a glycosaminoglycan isolated on a commercial basis from animal tissues and used in the clinic as an antithrombotic drug.

EP 0 509 120 B1 discloses the use of glycosaminoglycans, GAGs, for the preparation of a topical pharmaceutical composition for the prevention and therapy of diseases of the cervical vaginal area. As examples of said diseases are mentioned dystrophy and atrophy states induced by lack of estrogen hormones, vaginal dermatitis, a specific vaginitis etc. The GAGs are said to take part in the safeguarding and restoring of the natural vaginal ecosystem.

The glycosaminoglycans are described as belonging to a highly heterogeneous class of macromolecules having very long molecules containing repeating disaccharide units forming linear macromolecules. In general each of the repeating units comprises a residue consisting of an aminosugar, that is glucosamine or galactosamine, and a uronic acid residue consisting of glucuronic acid or iduronic acid. The hydroxyl group at $C_2$, $C_3$, $C_4$ and $C_6$ and the amino group on $C_2$ may be substituted by sulfate groups. The GAGs are represented by the following compounds: heparin, heparan sulfate, dermatan sulfate, hyaluronic acid, chondroitin sulfate, keratan sulfate.

EP 0 867 452 A1 refers to a cervical ripening agent which as an active ingredient contains hyaluronic acid or a derivative thereof.

It is well known that glycosaminoglycans have a multitude of effects on cell activity.

DESCRIPTION OF THE INVENTION

It has recently been found that the expression of heparan sulfate proteoglycans varies during the uterine remodeling during pregnancy and labor. They are thus believed to play a pivotal role in labor. It has also been found that treatment of human uterine strips with sulfated glycosaminoglycans enhances the contractile activity thereof.

The present invention refers to the use of sulfated glycosaminoglycans having an anticoagulant activity of 100 BP units/mg or less for the manufacture of a pharmaceutical preparation for prophylactic priming or curative treatment of the cervix and the myometrium for establishing effective labor in women. Normal labor includes a softening of the cervix and regular myometrial contractions.

The anticoagulation effect was evaluated by measuring the increase in clotting time per mg sulfated glycosaminoglycan, and is stated in BP units per mg. Heparin has an anticoagulant activity of 157 BP units/mg.

The sulfated glycosaminoglycans, that is mainly heparin, heparan sulfate, dermatan sulfate and chondroitin sulfate, are composed of alternating hexosamine and uronic acid residues. Hyaluronic acid has no sulfate groups. The presence of D-glucuronic acid (GlcA) and its C-5 epimer L-iduronic acid (IdoA) and the specific sulfation of hexosamines and uronosyl residues endow the polymer an extreme structural variation. The structure can range from none or very few to nearly 100% iduronic acid-containing disaccharides. The organization of GlcA- and IdoA-N-hexosamine containing disaccharides can vary from long blocks to an alternating disaccharide pattern. A high degree of sulfation and a high degree of iduronic acid sulfate generally involves a high biological activity of the compound. There are different well-defined polysaccharides of dermatan sulfate (DS), chondroitin sulfate (CS), heparan sulfate (HS) and depolymerised heparin.

Heparan sulfate, having glucosamine and uronic acid as repeating disaccharides and consisting of N-acetylated and N-sulfated disaccharides that are arranged mainly in a segregated manner, has ubiquitous distribution on cell surfaces and in the extracellular matrix. It is generally less sulfated and has a lower iduronate content than heparin and has a more varied structure. Interactions between heparan sulfate and proteins are implicated in a variety of physiological processes, such as cell adhesion, enzyme regulation, cytokine action, virus entry and anticoagulant properties. Heparan sulfates possess anticoagulant activity depending on the presence of a specific anticoagulant pentasaccharide, however considerably less than heparin. Heparan sulfate is a linear polysaccharide which can be prepared from porcine intestinal mucosa or from bovine lung, from heparin side fractions using cetylpyridinium chloride fractions and sequential salt extraction as described by Fransson et al., Structural studies on heparan sulphates, Eur. J. Biochem. 106, 59-69 (1980).

The invention refers to the use of a sulfated glycosaminoglycan, which belongs to the group consisting of heparan sulfates and depolymerised heparan sulfates.

Chondroitin sulfate is a sulfated linear polysaccharide consisting of alternating glucuronic acid and N-acetyl-galactosamine residues, the latter being sulfated in either 4 or 6 position. They can be prepared from bovine tracheal or nasal cartilage. CS is of importance for the organization of extracellular matrix, generating a interstitial swelling pressure and participating in recruitment of neutrophils.

The invention also refers to the use of chondroitin sulfates or depolymerised chondroitin sulfates.

Dermatan sulfate is a sulfated linear polysaccharide consisting of alternating uronic acid and N-acetylated galactosamine residues. The uronic acids are either D-GlcA or L-IdoA and the disaccharide can be sulfated in 4 and 6 and 2 on galactosamine and IdoA, respectively. DS can be prepared from porcine skin and intestinal mucosa. Dermatan sulfate possesses biological activities such as organization of extracellular matrix, interactions with cytokines, anticoagulant activities and recruitment of neutrophils.

The invention also refers to the use of dermatan sulfates or depolymerised dermatan sulfates.

Low molecular weight heparins or depolymerised heparins are linear oligosaccharides having a $M_r$ of between 2 and 10 kDa, mainly consisting of alternating N-sulfated glucosamine and IdoA residues and often containing the anticoagulant pentasaccharide. They can be prepared from heparins by specific chemical cleavage. Their main clinical function is to inhibit factor Xa, resulting in an antithrombotic effect. It is proposed to have antimetastatic properties. Fragmin® (Pharmacia, Sweden) is an example of a low molecular heparin obtained by controlled depolymerisation of heparin and having an antithrombotic effect owing to inhibition of factor Xa. Heparin fragments having selective anticoagulant activity, as well as methods for the preparation thereof, are described in U.S. Pat. No. 4,303,651. The anticoagulant effect is, however, normally not desirable for a preparation to be used during labor.

The invention especially refers to the use of a glycosaminoglycan which belongs to the group consisting of depolymerised heparins having a relative molecular weight below 10000 Da, preferably not higher than 6000 Da.

It is essential that the anticoagulant activity is not too high, and according to a preferred aspect the invention refers to the use of a sulfated glycosaminoglycan having an anticoagulant activity of 30 BP units/mg or less.

Tests in vitro suggest that low sulfated structures of low or no anticoagulative potency are preferred compounds. Thus side products obtained during manufacture of heparin are good candidates for selection of starting material. Compounds with the desired properties can be obtained from heparan and heparin side fractions using specific periodate oxidation to eradicate the antithrombin III binding properties.

Selective N-desulfation followed by re-N-acetylation, or selective O-desulfation also yields compounds with low anticoagulant activity.

Selective N-deacetylation followed by specific N- and/or O-sulfation also yields compounds of desired activity.

The invention especially refers to the use of a glycosaminoglycan having a sulfate/hexosamine ratio below 1.0 and an anticoagulant activity, or clotting time, less than 10 BP units/mg.

If the amount of endogenous oxytocin has reached its optimal level at the time for onset of labor, a pretreatment with the sulfated glycosaminoglycans to be used according to the invention will initiate the onset of labor. In case of an insufficient endogenous oxytocin level, the sulfated glycosaminoglycans can be used in a single dose in combination with i.v. oxytocin for the priming of the myometrium.

The invention also refers to the use of sulfated glycosaminoglycans for the manufacture of a pharmaceutical preparation which can be administered locally that is topically, such as by intracervical, vaginal, rectal, or dermal administration, or systemically that is parenteral, such as by subcutaneous or intravenous injection. The pharmaceutical composition can also be given by oral administration.

For parenteral administration the active compounds can be incorporated into a solution or suspension, which also contain one or more adjuvants such as sterile diluents such as water for injection, saline, fixed oils, polyethylene glycol, glycerol, propylene glycol or other synthetic solvents, antibacterial agents, antioxidants, chelating agents, buffers and agents for adjusting the tonicity. The parenteral preparation can be delivered in ampoules, disposable syringes or as infusions.

A topical preparation consists of the active sulfated glycosaminoglycans in combination with a conventional pharmaceutically acceptable carrier. The carrier or excipient can be a solid, semisolid or liquid material that can serve as a vehicle for the active substance. Examples of topical preparations are an ointment, cream, gel, nasal or vaginal spray, lotion, solution or suspension.

In order to bring about an effective labor the sulfated glycosaminoglycans can be administered in a single dose every 24 h for a period of 1-30, preferably 1-10 days. The dose must be estimated as the lowest dose giving myometrial contractions. An estimated single dose is 25-100 mg/d, but may be up to 1 g or more. The dose is related to the form of administration.

EXAMPLES

Example 1

Preparation of Heparan Sulfates 10 g of the heparin by-product, TB 001-91 SVCM 950130 (Kabi-Pharmacia, Sweden) was dissolved in 1 l of 5% calcium acetate—0.5 M acetic acid. The solution was filtered. The filtered solution was then adjusted to an ethanol concentration of 18%. The supernatant after centrifugation was then adjusted to an ethanol concentration of 36%. The precipitate was collected by centrifugation. The following heparan sulfates were prepared in accordance with Fransson et al., Structural studies on heparan sulphates, Eur. J. Biochem. 106, 59-69 (1980).

Preparation of HS6

The precipitate obtained between 18 and 36% ethanol was dissolved in 1.2 M of NaCl. 18 g of cetylpyridinium chloride, CPC, was added and a precipitate was allowed to develop for 24 h. The precipitate was recovered by filtration and redissolved in 2 M NaCl. The filtrate was used for the preparation of HS5. To the resolved precipitate 3 volumes of ethanol was added. The resulting precipitate was allowed to develop for 16 h and the collected by centrifugation. Finally it was redissolved in water and reprecipitated with 3 volumes of ethanol—0.4% of sodium acetate. The precipitate was collected by centrifugation and dried. The yield was 4.34 g.

Preparation HS5

The filtrate from the preparation of HS6 was then diluted with 0.1% CPC to a final concentration of 1.0 M NaCl. It was then treated as in HS6. The filtrate was used for the preparation of HS4. The yield was 0.82 g.

Preparation of HS4

The filtrate from the preparation of HS5 was then diluted with 0.1% CPC to a final concentration of 0.8 M NaCl. It was then treated as in HS6. The filtrate was used for the preparation of HS3. The yield was 0.51 g.

Preparation of HS3

The filtrate from the preparation of HS4 was then diluted with 0.1% CPC to a final concentration of 0.6 M NaCl. It was then treated as in HS6. The filtrate was used for the preparation of HS2. The yield was 0.17 g.

Preparation of HS2

The filtrate from the preparation of HS3 was then diluted with 0.1% CPC to a final concentration of 0.4 M NaCl. It was then treated as in HS6. The yield was 0.09 g.

The different heparan sulfates were analysed as to the content of glucuronic acid, iduronic acid, and total sulfate groups. The number of sulfate groups on the amino group of the hexosamine was determined as mole per mole, and the percentage of iduronic acid residues was determined. The results are given in Table 1 below. The anticoagulant activity was also evaluated by measuring the clotting time per mg heparin sulfate, and stated in BP units per mg in Table 1 below.

TABLE 1

| | Analysis of heparan sulfates | | | | |
|---|---|---|---|---|---|
| Preparation | Sulfate/hexosamine (mole/mole) | N-sulfate/hexosamine (mole/mole) | IdoA/total uronic acid (%) | IdoA-SO$_4$/total uronic acid (%) | Anticoagulant activity (BP units/mg) |
| HS2 | 0.56 | 0.26 | 30 | 10 | — |
| HS3 | 1.00 | 0.40 | 35 | 20 | 8 |
| HS4 | 1.15 | 0.47 | 40 | 25 | 30 |
| HS5 | 1.23 | 0.62 | 50 | 45 | 88 |
| HS6 | 1.63 | 0.73 | 65 | 60 | 140 |

The anticoagulant activity of all the heparan sulfate preparations above can be abrogated by selective periodate oxidation, see Fransson L A, and Lewis W. Relationship between anticoagulant activity of heparin and susceptibility to periodate oxidation, FEBS Lett. 1979, 97:119-23.

Example 2

Preparation of Dermatan Sulfate

One kg of dried pig skin was suspended in 5 l of 0.5 M of NaCl, 0.01 M EDTA and 0.01 M of cysteine hydrochloride, pH 6.5. 500 mg of crystalline papain was added and the digestion was allowed to proceed for 50 h. The digest was filtered and then precipitated with 75 ml of a 10% solution of CPC. The resulting pyridinium complex was collected by filtration and the redissolved in 2M NaCl containing 15% of ethanol. This solution was diluted with 3 volumes of 0.5% CPC. The precipitate was collected and dissolved in 200 ml 1 M of NaCl and 40 ml of ethanol. The material was redissolved in 100 ml of water and then precipitated with 3 volumes of ethanol—0.4% sodium acetate. The resulting precipitate was collected and dried. The final yield was 2.32 g. See Fransson et al., Structure of pig skin dermatan sulfate. 1. Distribution of D-glucuronic acid residues. (1971) *Eur. J. Biochem.* 18, 422-430.

Preparation of Ds with Different Content of L-Iduronic Acid 2.2 g of the material obtained above was dissolved in 220 ml of 5% calcium acetate—0.5 M acetic acid. This solution was mixed with ethanol and the precipitates formed between 0-18% ethanol (DS-18), 18-36% ethanol (DS-36), and 36-50% ethanol (DS-50), respectively, were collected. The materials were redissolved in water and reprecipitated with 3 volumes of ethanol—0.4% sodium acetate. After drying the final yield was 0.9 g for DS-18; 1.02 g for DS-36; 0.28 g for DS-50.

The different dermatan sulfates were analyzed as to content of sulfate groups, glucuronic acid, iduronic acid and hexosamine, and the results are presented in Table 2 below.

TABLE 2

| | Analysis of dermatan sulfates | | |
|---|---|---|---|
| Preparation | Sulfate/hexosamines (mole/mole) | IdoA/total uronic acid (%) | IdoA-SO$_4$/total uronic acid (%) |
| DS-18 | 1.16 | 90 | 20 |
| DS-36 | 1.12 | 75 | 15 |
| DS-50 | 1.06 | 50 | 10 |

The DS preparations contain 99% galactosamine of total hexosamin and the HS and heparin preparations contain >97% glucosamine of total hexosamine.

Experimental

Test 1

Contractile Assay

In the following test heparan sulfate HS2 and HS6 obtained from the heparin side fraction TB 001-91 SVCM 950130 (Kabi-Pharmacia, Sweden) were tested. HS6 differs from HS2 by being more highly sulfated and having more L-iduronic acid residues (see Table 1 above).

Uterine samples were obtained from women undergoing elective caesarian section at 38-39 weeks of gestation. The samples measured 20×10×10 mm and were taken from the upper part of the isthmic incision. The biopsy was immediately placed in ice-cold Krebs-Ringer buffer. The biopsies were cut into longitudinal strips, length 10-15 mm and breadth about 5 mm. The strip was mounted vertically in an organ bath of 37° C. containing 2 ml Krebs-Ringer solution. The solution was bubbled with a mixture of 95% $O_2$ and 5% $CO_2$ in order to maintain a pH in the bath of 7.35-7.45. Experiments were carried out after the strips had equilibrated to a stable contractile state, usually within 1-2 h after mounting. The contractions were recorded isometrically with a Grass model 7 polygraph (Grass Instr. Co., Quincy, Mass., USA). All samples were exposed to 100 mM KCl during the experiment in order to get a standardized maximum response. Different doses of heparan sulfate were then added to the bath containing the uterine strip. After 20 min 1 U oxytocin was added. Addition of 1 U oxytocin only was used as a control.

This procedure was repeated using 6 μg of heparan sulfate. After 20 min 1 unit of oxytocin was added. The contractions were recorded and evaluated by integrating the surface under the curve. Two heparan sulfates, HS2 and HS6, with different structure was added and as control 1 unit of oxytocin was used. See Table 3 below.

TABLE 3

Relative contractility of myometrial strip after stimulation with heparan sulfate and oxytocin, in % of unstimulated control

|  | Unstimulated control | Oxytocin control, 1 U | HS | HS and oxytocin |
|---|---|---|---|---|
| HS2 | 100 | 226 | 289 | 936 |
| HS6 | 100 | 226 | 183 | 584 |

The combination of oxytocin and HS6 resulted in a 2.5 fold increase of contractile force and the combination with HS2 gave a 4.1 fold increase in contractile force.

This shows that heparan sulfate enhances the contractile force of human uterine strips in vitro. The effect is dependent on the heparan sulfate structure, and a low sulfated structure appears to be more effective.

When this test was repeated with dermatan sulfate, DS-18, see Table 2, contractility was registered, but the results have not yet been evaluated.

Test 2

Effect on $Ca^{2+}$ Levels in Cervical Fibroblasts

Fibroblast cultures were established from non-pregnant, and term pregnant patients and from women delivered vaginally (after partus patients). The cells were cultured in monolayer cultures with minimum essential medium with 10% donor calf serum. For experiments these cells were plated on cover glasses with at semi-confluence and loaded with Fluo-4 in phosphate buffered saline containing 10 mM HEPES for 30 min. Initially phosphate buffered saline containing 10 mM HEPES (HEPES-buffer) was pumped into the observation chamber for 30 s, then KCl in the same buffer was pumped for 60 s followed by HEPES-buffer for 30 s. Then 10 ng of PDGF/ml in HEPES-buffer was added. The fluorescence was monitored continuously for 3 min. In other experiments PDGF was replaced with 100 μg of HS6. No change of fluorescence was noted in cultures established from non-pregnant and term pregnant patients. In cultures obtained from patients directly after partus KCl, PDGF and HS6 all induced a transient 4-8 fold increase of fluorescence, which demonstrates a transient increase of intracellular $Ca^{2+}$. This demonstrates that cells in cultures established from patients after partus are activated by HS6. This effect is postulated to be of importance at partus for final preparation of cervix for delivery.

Test 3

Clinical Test With Dalteparin Sodium Salt (FragMin®)

Clinical data on delivery outcome in nulliparous women have been studied. 14 nulliparous women were given Fragmin® (Pharmacia, Sweden) subcutaneous during pregnancy due to an increased risk of thrombosis. The administered prophylactic dose was 5000 IE daily in all but 4 women who had 2500 IE daily. Eight of the women were treated more than 12 weeks (range 12-28 weeks) and 6 of them during 1-6 weeks. As matched controls served the next 13 nulliparous women without Fragmin® medication giving birth in the same clinic immediately after the women included in the study. Endpoints were labor-delivery time (hour) and number of caesarian sections and their indications.

No correlation could be found between the duration of the treatment and the duration of the parturition. The labor—delivery time turned out to be 5.8±2.6 h in the patient group and 14.0±6.3 h in the control group (p<0.001). Furthermore slow progress of labor was reported in 6 out of 13 subjects in the control group compared to 1 of 14 in the treatment group.

The number of caesarian sections was 3 in each group, but the indications in the study group were pre-ecklampsia, insufficient analgesia and suspected fetal asphyxia. In the control group all 3 had the main indication arrest of labor, in two women in combination with suspected fetal asphyxia.

The labor-delivery time has also been investigated in 21 parous women which had been given Fragmin® as above in comparison to 9 controls. The labor-delivery time in the group given Fragmin® was 3.5±2.9 h (range 0.5-8) compared to 5.9±2.1 h (range 3-12) in the control group (p<0.05). The labor-delivery time was thus significantly lower in the medicated group.

The invention claimed is:

1. A method for priming or treating the cervix and the myometrium for establishing effective labor in a woman, comprising the step of:

administering to a pregnant woman for a period of 1 to 30 days an effective amount of at least one sulfated glycosaminoglycan selected from the group consisting of heparan sulfate, depolymerised heparan sulfate, dermatan sulfate, depolymerised dermatan sulfate, low molecular weight heparin and depolymerised heparin, said at least one sulfated glycosaminoglycan having an anticoagulant activity of 100 BP units/mg or less, wherein the effective amount is sufficient to increase contractility of the pregnant woman's myometrium and/or increase cervical ripening, wherein the pregnant woman does not suffer any complication requiring antithrombotic therapy with sulfated glycosaminoglycans.

2. The method according to claim 1, wherein the at least one glycosaminoglycan comprises at least one glycosaminoglycan selected from the group consisting of heparan sulfate and depolymerised heparan sulfate.

3. The method according to claim 1, wherein the at least one glycosaminoglycan comprises at least one glycosaminoglycan selected from the group consisting of dermatan sulfate and depolymerised dermatan sulfate.

4. The method according to claim 1, wherein the at least one glycosaminoglycan comprises depolymerised heparin having an average molecular weight below 10 000 Da.

5. The method according to any one of claim 1, 2, 3, or 4, wherein the at least one glycosaminoglycan has an anticoagulant activity of 30 BP units/mg or less.

6. The method according to claim 1, wherein the at least one glycosaminoglycan has a sulfate/hexosamine ratio below 1.0 and an anticoagulant activity of 10 BP units/mg or less.

7. The method according to claim 1, wherein the at least one glycosaminoglycan is administered in combination with oxytocin.

8. The method according to claim 1, wherein the at least one glycosaminoglycan is administered topically in a topical pharmaceutical preparation.

9. The method according to claim 1, wherein the at least one glycosaminoglycan is administered in a parenteral pharmaceutical preparation.

10. The method according to claim 4, wherein the at least one glycosaminoglycan comprises depolymerised heparin having a molecular weight not higher than 6,000 Da.

11. The method according to claim 1, wherein the complication requiring antithrombotic therapy is vein thrombosis or preeclampsia.

12. The method according to claim 1, wherein the effective amount is sufficient to increase contractility of the pregnant woman's myometrium and increase cervical ripening.

* * * * *